United States Patent [19]

Koerner et al.

[11] Patent Number: 4,501,911

[45] Date of Patent: Feb. 26, 1985

[54] ORGANOSILICON-MODIFIED POLYDIENES, PROCESS FOR THEIR SYNTHESIS AND THEIR USE AS EMULSION BREAKERS FOR CRUDE OIL

[75] Inventors: Götz Koerner; Christian Weitemeyer, both of Essen, Fed. Rep. of Germany

[73] Assignee: Th. Goldschmidt AG, Essen, Fed. Rep. of Germany

[21] Appl. No.: 515,369

[22] Filed: Jul. 19, 1983

[30] Foreign Application Priority Data

Jul. 28, 1982 [DE] Fed. Rep. of Germany ....... 3228135

[51] Int. Cl.³ ............................ C07F 7/08; C07F 7/18
[52] U.S. Cl. .................................. 556/446; 556/435; 556/438; 208/188; 252/358
[58] Field of Search ........................ 556/435, 438, 446; 208/188; 252/358

[56] References Cited

U.S. PATENT DOCUMENTS 3,481,966 12/1969 Stuart .............................. 536/446 X
4,396,751 8/1983 Kampf et al. .................... 556/446 X Primary Examiner—Paul F. Shaver
Attorney, Agent, or Firm—Toren, McGeady and Stanger

[57] ABSTRACT

Organosilicon-modified polydienes having the formula:

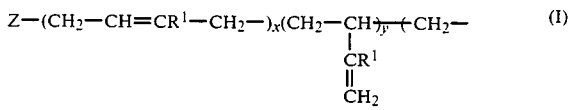

(I)

-continued

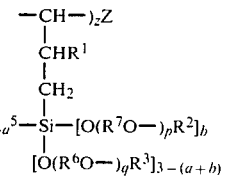

in which
Z represents a chain terminating group,
$R^1$ is a hydrogen or methyl radical,
$R^2$, $R^3$, and $R^4$ are lower alkyl radicals with 1 to 4 carbon atoms, which can be the same or different within the polymeric molecule,
$R^5$ is a methyl radical or the $O-(R^8O-)_s-R^4$ group;
$R^6$, $R^7$, $R^8$ are alkylene radicals with 2 to 4 carbon atoms,
C:O ratio of
$R^6O$ is 2.25 to 3:1,
$R^7O$ is 2 to 2.75:1,
$R^8O$ is 2 to 3:1 however, the difference between the C:O ratio of $R^6O$ and $R^7O$ must be at least 0.25, and the C:O ratio of $R^8O$ must be less than that of $R^7O$ or greater than that of $R^6O$,
a is 0 to 2,
$0<b<3$, whereby $0<a+b<3$,
p, q, $s \geq 2$,
x, $y \geq 0$, and
$z \geq 3$.

The invention furthermore relates to a process for the synthesis of these compounds as well as to their use as emulsion breakers for crude oil/water emulsions.

10 Claims, No Drawings

ORGANOSILICON-MODIFIED POLYDIENES, PROCESS FOR THEIR SYNTHESIS AND THEIR USE AS EMULSION BREAKERS FOR CRUDE OIL

BACKGROUND OF THE INVENTION

1. Field of the Invention

This invention pertains to novel emulsion breakers based on organosilicon-modified polydienes.

2. Description of the Prior Art

A large portion of the crude oil produced contains lesser or greater amounts of salt water in emulsified form. Such emulsions, which occur predominantly as water-in oil emulsions, must be separated into their phases since the salt water contained in the emulsion would interfere with the further processing of the oil, especially during transport and distillation.

The separation of such crude oil emulsions into their component phases is accomplished either by allowing the emulsions to settle under gravity, by heat treatments, by centrifuging, by applying an electrical potential, by adding emulsion breakers, or by a combination of several of these methods. However, the crude oil emulsions produced are generally too stable to be broken by sedimentation, filtration, centrifugation or heating alone. On the other hand, small concentrations of emulsion breakers are sufficient to cause an emulsion to coalesce.

A large number of emulsion breakers have already been proposed. This is largely due to the fact that the different crude oils have different compositions and that emulsion breakers which are suitable for crude oils originating from one place, are unsuitable for crude oil emulsions from a different production site. The known emulsion breakers can only be used for specific crude oils.

Typical emulsion breakers include alkyl sulfates and alkylaryl sulfonates, as well as petroleum sulfonates, in the form of their amine salts. Also suitable are products of the addition reaction of ethylene oxide with suitable compounds having active hydrogen atoms, such as, for example, alkylphenols, castor oil, fatty acids, fatty alcohols, alkylphenols and aldehyde resins. Relevant information may be found, for example, in the book "Oberflächenaktive Anlagerungsprodukte des Ethylenoxids" (Surface Active Addition Products of Ethylene Oxide) by N. Schönfeld, Wissenschaftliche Verlagsgesellschaft mbH, Stuttgart, 1959, page 295.

German Pat. No. 19 37 130 discloses certain known polyoxyalkylene-polysiloxane block copolymers which have outstanding properties as emulsion breakers for crude oil emulsions of the water-in-oil type originating from very different locations. These copolymers act in very low concentrations as emulsion breakers, that is, in concentrations which are less than those at which the products of the state of the art are effective. The polyoxyalkylene-polysiloxane block copolymers have polyoxyalkylene blocks with a molecular weight of 500 to 4,000 which consist of polyoxyethylene and polyoxypropylene blocks in a weight ratio of 40:60 to 100:0. The polysiloxane blocks have 3 to 50 silicon atoms per block.

German Pat. No. 22 50 920 discloses mixtures of 0.2 to 30 weight percent of the aforementioned polyoxyalkylene-polysiloxane block copolymers with 70 to 99.8 weight percent of silicon-free emulsion breakers. These are products of the alkylene oxide addition reaction with organic compounds having reactive hydrogen atoms. Particular products of this type are the reaction products of alkylene oxides with alkylphenolaldehyde resins, block and random copolymers of propylene and ethylene oxide, their reaction products with dicarboxylic acids or diisocyanates, as well as mixtures of these products. In this connection, it was noted that the mixtures conforming to the disclosure of German Pat. No. 22 50 920 have particularly advantageous properties in respect to breaking emulsions and, at the same time, preventing foaming.

German Pat. No. 23 21 557 discloses silicon-containing block copolymers based on organosilicon-modified polydienes. These compounds are obtained by the addition reaction of silanes containing hydrogen radicals with polydienes. The silanes may have additional halogen, alkoxy or acyloxy radicals which are then reacted with polyethers. These compounds have many uses, for example as additives in the manufacture of polyurethane foams, release agents, and preparation agents in the textile industry or in cosmetics. The use of the compounds as emulsion breakers in coalescing crude oil/water emulsions has been mentioned.

German Offenlegungsschrift No. 1 620 934 discloses a process for the synthesis of organosilicon polymers which have a polybutadiene whose chain contains at least one unit of the following general formula

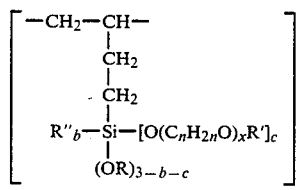

in which
R and R'' are hydrocarbyl radicals or substituted hydrocarbyl radicals,
$R'$ is a hydrocarbyl radical or a substituted hydrocarbyl radical or an acyl group,
b is 0, 1 or 2,
c is 1, 2 or 3,
b+c is not larger than 3,
n is 2, 3 or 4, and
x is a whole number between 2 and 100.
In this process, a low molecular polybutadiene is reacted with a compound of the general formula

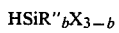

in which R'' and b have the above-given meanings and X represents a halogen atom or an OR group, wherein R has the meaning given above, and the product is subsequently reacted with a monohydroxy polyoxyalkylene ether. The compounds prepared according to the process of this German Offenlegungsschrift have surface active properties and are recommended as additives for the production of polyurethane foams.

SUMMARY OF THE INVENTION

We have discovered that compounds whose structure is similar to that of the products of German Offenlegungsschrift No. 1 620 934, but which differ from these when certain conditions are adhered to, have a significantly improved surface active effect and are especially suitable for breaking an emulsion of crude oil and water, particularly when the water in the oil contains varying amounts of dissolved salts.

The compounds of the present invention have the formula $$Z-(CH_2-CH=CR^1-CH_2-)_x(CH_2-CH)_y-(CH_2-CH-)_zZ$$

with side groups:

$$\begin{array}{cc} CR^1 & CHR^1 \\ \parallel & \mid \\ CH_2 & CH_2 \\ & \mid \\ & R_a^5-Si-[O(RO-)_pR^2]_b \\ & \mid \\ & [O(RO-)_qR^3]_{3-(a+b)} \end{array}$$

in which

Z represents a chain terminating group,
$R^1$ is a hydrogen or methyl radical,
$R^2$, $R^3$, $R^4$ are lower alkyl radicals with 1 to 4 carbon atoms, which can be the same or different within the polymeric molecule,
$R^5$ is a methyl radical or the $[O-(R^8O-)_s-R^4]$,
$R^6$, $R^7$, $R^8$ are alkylene radicals with 2 to 4 carbon atoms,
a is 0 to 2,
$0 < b < 3$, whereby $0 < a+b < 3$,
p, q, s $\geq 2$,
x, y $\geq 0$, and
z $\geq 3$ and wherein the C:O ratio of $R^6O$ is 2.25 to 3:1, the C:O ratio of $R^7O$ is 2 to 2.75:1, the C:O ratio of $R^8O$ is 2 to 3:1, the difference in the C:O ratio of $R^6O$ and $R^7O$ is not less than 0.25 and the C:O ratio of $R^8O$ is less than that of $R^7O$ or greater than that of $R^6O$.

DESCRIPTION OF THE PREFERRED EMBODIMENT

Examples of the chain terminating groups Z are: —H, $CH_2=CH-CH_2-CH_2-$, $-CH_2-CH_2-OH$, —COOH, —$CH_3$, —$C_4H_9$, —$C_6H_5$, —$CH_2-C_6H_5$, and —$Si(CH_3)_3$. A selection is made from these groups on the basis of the synthesis method employed.

The $R^2$, $R^3$ and $R^4$ radicals may also be branched or unsaturated.

A particular aspect of the invention is that rather than just one type of polyoxyalkylene block, at least two different types of polyoxyalkylene blocks are linked to the silicon atoms which are in the side branches of the polymeric molecule. These polyoxyalkylene blocks differ in their hydrophilic or hydrophobic character. Their hydrophilicity or hydrophobicity is determined by the C:O ratio of the alkylene oxide block. Since the polyoxyalkylene blocks are built up of alkylene oxide units with 2 to 4 carbon atoms, preferably of ethylene oxide and/or propylene oxide units, a lower value of the C:O ratio produces a hydrophilic character and a higher value of the C:O ratio a hydrophobic character. If the value of the C:O ratio is 2, it means that the polyoxyalkylene block consists exclusively of ethylene oxide units. A value greater than 2 means that the polyoxyalkylene block contains propylene oxide and possibly butylene oxide units in proportion to the value of the ratio.

Because of the condition that the difference in the C:O ratio of $R^7O$ and $R^6O$ must be at least 0.25, the alkylene oxide block with the $R^7O$ groups is always more hydrophilic than the polyoxyalkylene block with the $R^6O$ groups. Accordingly, relatively hydrophilic polyoxyalkylene blocks are present next to hydrophobic polyoxyalkylene blocks in the average polymeric molecule. Such an arrangement is responsible for the special surface active properties of inventively modified polydienes.

It is clear to those skilled in the art that, due to the synthesis method and catalysts employed, the polyoxyalkylene blocks are always mixtures of different chain lengths. The condition that the C:O ratio of the two polyoxyalkylene blocks must differ by at least 0.25 is, however, of decisive importance. This condition must be fulfilled even when the $R^6O$ or $R^7O$ is formed from a mixture of several polyoxyalkylene blocks.

By definition, the minimum difference in the C:O ratio of $R^6O$ or $R^7O$ is 0.25. The higher the C:O ratio of $R^6O$, the more advantageous it is to select a larger difference in the C:O ratio of $R^6O$ and $R^7O$. If the C:O ratio of $R^6O$ is 3, the C:O ratio of $R^7O$ cannot be more than 2.75. Preferably, however, it is less and has, for example, the value of 2.5.

The inventive compounds may contain more than two polyoxyalkylene blocks, since the substituent $R^5$ may be the $[O-(R^8O-)_s-R^4]$. Since C:O ration of $R^8O$ must, by definition, be smaller than that of $R^7O$ or larger than that of $R^6O$, the difference in the hydrophilic character of the other two polyoxyalkylene blocks is retained. If the C:O ratio of $R^7O=2$ and the C:O ratio of $R^6O=2.25$, the C:O ratio of $R^8O$ must be greater than 2.25 since it cannot be less than 2. If, for example, the C:O ratio of $R^7O=2.5$ and that of $R^6O=2.8$, the C:O ratio of $R^8O$ can be less than 2.5 or greater than 2.8.

The alkylene oxide units which form the polyoxyalkylene block may be randomly distributed or arranged in blocks.

Preferred compounds are those in which the units, having unsubstituted double bonds and labelled with the subscripts x and y, are present in an amount of 25 to 80 mole percent of the sum of the units $x+y+z$.

The following are examples of compounds in accordance with the invention:

$$C_4H_9-[CH_2-CH-]_{40}[CH_2-CH-]_{20}H$$

with side groups:

$$\begin{array}{cc} CH & CH_2 \\ \parallel & \mid \\ CH_2 & CH_2 \\ & \mid \\ & CH_3-Si-O-(R^7O-)_{36.9}C_4H_9 \\ & \mid \\ & O-(R^6O-)_{33.8}C_4H_9 \end{array}$$

C:O ratio of $R^6O=2.5:1$,
C:O ratio of $R^7O=2.2:1$;

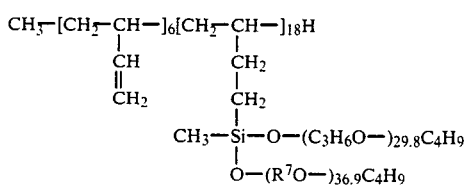

C:O ratio of $R^6O = 3:1$,
C:O ratio of $R^7O = 2.2:1$;

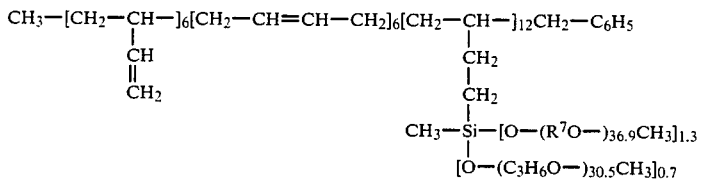

C:O ratio of $R^6O = 3:1$,
C:O ratio of $R^7O = 2.2:1$;

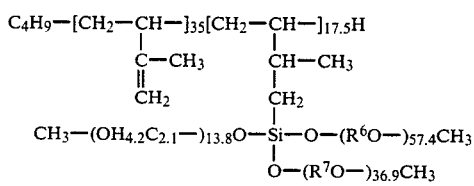

C:O ratio of $R^6O = 2.5:1$,
C:O ratio of $R^7O = 2.2:1$.

The present invention further comprises a method for synthesizing the new compounds having the formula

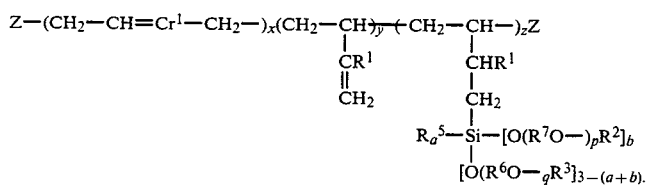

This is accomplished by adding at least z moles of silanes having the formula $$(CH_3)_a SiHX_{3-a} \qquad II$$

in which X is a halogen, alkoxy or acyloxy radical, by conventional procedures to polydienes having the formula

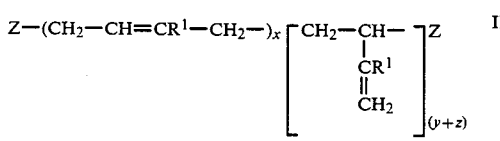

which have a molecular weight of 300 to 200,000. This reaction is carried out in the presence of noble metal catalysts. The addition products obtained are reacted by a known procedure with a mixture which consists of at least two polyoxyalkylene monools and which contains b . z moles of an optionally trimethylsilylated polyoxyalkylene monool having the formula $$HO(R^7O—)_p R^2 \qquad IV$$

and (3-a-b)z moles of an optionally trimethylsilylated polyoxyalkylene monool having the formula $$HO(R^6O—)_q R^3 \qquad V$$

or consecutively with these optionally trimethylsilylated polyoxyalkylene monools.

The aforementioned $R^1$, $R^2$, $R^3$, $R^4$ and Z radicals, as well as the subscripts a, b, p, q, s, x, y and z have the already given meaning.

When $R^5$ represents a polyoxyalkylene block, a . z moles of a monool having the formula $$HO(R^8O—)_s R^4 \qquad VI$$

must be added to and similarly reacted in the mixture or in the stepwise reaction. The trimethylsilyl derivative of the monool VI may also be used in the same manner.

The process of the present invention may be carried out in much the same way as the process described, for example, in German Pat. No. 23 21 557. As catalysts for the addition reaction of silanes of formula II to polydienes of formula III, platinum catalysts are preferably used, such as, for example, hexachloroplatinic acid, or platinum ethylene pyridine dichloride. The reaction is advisably carried out in the presence of a solvent, especially toluene. The addition reaction of the silane to the polydiene is carried out preferably at elevated temperatures, for example, at the boiling point of toluene.

The intermediates obtained are now reacted in the amounts given above with polyoxyalkylene monools of formula IV, V and optionally VI either in the form of their mixture or consecutively. This reaction also is advisably run in the presence of a solvent, toluene once again being preferred. However, other inert solvents, such as, for example, methylene chloride, glycol ethers or cyclic ethers may also be used. If X represents a halogen radical, the hydrogen halide released is appropriately collected in ammonia. An amine can also be used instead of ammonia. When X represents an acyloxy radical, the carboxylic acid released can be neutralized in a similar manner. Should X represent an alkoxy radical, it is advisable to remove the low molecular alcohol released from the reaction mixture by distillation. For this reason, the methoxy or ethoxy radical is preferred as the alkoxy radical.

In a process in accordance with the present invention which is useful especially with polyoxyalkylene compounds which are difficult to dry, the polyoxyalkylene monools of formulas IV and V, as well as optionally VI, are reacted with more than molar amounts of trimethylchlorosilane, before they are reacted with the products of the addition reaction between compounds of formulas II and III. In so doing, any water present is converted into hexamethyldisiloxane and hydrogen chloride and the OH group of the monools of formulas IV and V, as well as optionally VI, is trimethylsilylated. In the final conversion to the claimed compounds of formula I, a trimethylsilyl compound is then split off.

The inventive emulsion-breaking agents are preferably added to the crude oil/water emulsions in amounts of 1 to 300 ppm. It is also possible to dissolve the inventive compounds in a solvent, such as, toluene for example, and to add the solution to the crude oil. The compounds lead to a rapid and almost complete separation of water from the crude oil. The compounds do not interfere with the further processing of the oil and especially do not lead to form problems during the distillation or when the oil is being worked up.

To those skilled in the art, it is clear that the inventive compounds, like those described in German Pat. No. 23 21 557, can also be used for other purposes, for example, as cell regulating agent for polyurethane foams, as a release agent, as a finishing agent in the textile industry and for cosmetic purposes. Quite generally, the products can be used where lowering the surface tension, especially of water, is important.

The following examples illustrate the present invention:

EXAMPLE 1

Polybutadiene (54 g), with a molecular weight of 1,200 and a vinyl group content of more than 85 mole percent, is dissolved in an equal amount of toluene and mixed with 10.8 mg of platinum ethylene pyridine dichloride. Methyldichlorosilane (69 g) is added dropwise at 100° C. and the solution is kept for a further 3 hours at 100° C. Subsequently, the volatile compounds are distilled off under vacuum at 80° C. A brown, highly viscous substance (119 g), with an acid value of 9.53 meq acid/g, corresponding to a conversion of 0.57 butadiene units is obtained.

1890 g of a 1:1 mixture of the polyoxyalkylene monools $C_4H_9-(O-R^7)_{36.9}OH$ and $C_4H_9-(O-R^6)_{33.8}OH$ (C:O ratio of $R^7O=2.2:1$; of $R^6O=2.5:1$) are dissolved in 1890 g of toluene and mixed with 111 g of triethylamine as well as 210 g of a 50% solution of the previously prepared polybutadiene/methyldichlorosilane adduct in toluene. The mixture is heated and refluxed for 4 hours and then filtered. Volatile components are removed under vacuum at 80° C. and the residue is filtered once more. A yellowish liquid (1,750 g) with a viscosity of 5,400 mpa×sec at 25° C. is obtained. Gel permeation chromatography shows that the liquid has only a slight free polyether content and consists essentially of a high molecular weight substance (peak molecular weight=43,000 based on polystyrene) of the formula given in the claim. The formula is verified by the following analytical data:

Elementary analysis: Found: Si 0.6%; C 59.0%; Calculated: Si 0.7%; C 58.4%.

| Characteristic IR bands: | |
| --- | --- |
| Si—O—C | 1090 cm$^{-1}$ |
| Si—CH$_3$ | 1255 cm$^{-1}$ |
| vinyl | 910 cm$^{-1}$ |

Iodine number: 6 $\left[ \dfrac{g/2 \times 100}{g \text{ of substance}} \right]$

EXAMPLE 2

As in Example 1, 54 g of a polybutadiene with a molecular weight of 3,000 and a vinyl content of more than 90% are reacted with 4.8 mg of platinum ethylene pyridine dichloride and 37.9 g of methyldichlorosilane to form 87 g of a product which contains 6.6 meq of acid/g. This corresponds to a conversion of 0.29 butadiene units of the polybutadiene.

The synthesis procedure is continued as in Example 1 by reacting 945 g of $C_4H_9-(O-R^7)_{36.9}OH$ and $C_4H_9(O-R^6)_{29.8}OH$ (C:O ratio of $R^7O=2.2:1$; of $R^6O=3:1$) in the ratio of 3:1 as the polyether mixture with 152 g of a 50% solution of the previously synthesized polybutadiene/methyldichlorosilane adduct in toluene. A yellowish liquid (911 g) is obtained with a viscosity of 6,830 mPa×sec. By GPC, this liquid is shown to have only a slight content of free polyether. It consists essentially of a high molecular weight substance (PMW 57,000) of the formula given in the claim. The formula is verified by the following analytical data:

Elementary analysis: Found: Si 0.6%; C 59.8%; Calculated: Si 0.7%; C 59.4%.

| Characteristic IR bands: | |
| --- | --- |
| Si—O—C | 1090 cm$^{-1}$ |
| Si—CH$_3$ | 1255 cm$^{-1}$ |
| vinyl | 910 cm$^{-1}$ |

Iodine number: 16

EXAMPLE 3

The procedure of Example 2 is followed with the difference that 682 g of $C_4H_9-(O-R^7)_{36.9}OH$ and $C_4H_9-(O-R^6)_{12.5}OH$ (C:O ratio of $R^7O=2.2:1$; of $R^6O=3:1$) in a 1:1 molar ratio are used as the polyether mixture.

Yield: 659 g; PMW: 43,000.

Elementary Analysis: Found: Si 0.8%; C 60.1%; Calculated: Si 1.0%; C 60.0%.

IR bands as in Example 2.

Iodine number: 21

EXAMPLE 4

A polybutadiene (54 g), with a molecular weight of 151,000 and a vinyl group content of more than 90% is reacted as a 10% solution in toluene with 36.3 mg of platinum ethylene pyridine dichloride and 57.5 g of methyldichlorosilane for 1 hour at 70° C. Subsequently, five 100 ml portions of methylene dichloride are added and the volatiles are distilled off at atmospheric pressure in order to remove unreacted methyldichlorosilane. The toluene solution obtained is titrated and found to have 5.7 meq acid/g of solid, which corresponds to a conversion of 0.23 butadiene units.

This compound (80 g) is reacted with 865 g of the same polyether mixture and under the same conditions used in Example 1. A yellow-brown, highly viscous liquid (811 g), having the following analytical data, is obtained:

Elementary analysis: Found: Si 0.6%; C 60.0%; Calculated: Si 0.7%; C 59.5%.

IR bands as in Example 2.

Iodine number: 19

EXAMPLE 5

A polyisoprene (6.8 g) with a molecular weight of 36,000 and with more than 90% 3,4-units, which was synthesized from isoprene and butyl lithium, was enclosed as a 20% solution in toluene together with 5.8 g of methyldichlorosilane and 3.9 mg of hexachloroplatinic acid in a pressure vessel and heated for 8 hours at 70° C. After removal of the volatile components at atmospheric pressure, 11.3 g of a dark, highly viscous substance, with an acid value of 6.9 meq acid/g, is obtained. This corresponds to a conversion of 0.39 isoprene units.

This compound is reacted with 140 g of the same polyether mixture and under the same conditions used in Example 1. A brown liquid (108 g) with a viscosity of 12,370 mPa×sec, is obtained. Gel permeation chromatography shows that the liquid contains only slight amounts of unreacted polyether and consists essentially of a high molecular weight substance of the formula given in the claim. The formula was verified by the following analytical data:

Elementary analysis: Found: Si 0.5%; C 59.4%; Calculated: Si 0.7%; C 59.0%.

| Characteristic IR bands: | |
|---|---|
| Si—O—C | 1090 cm$^{-1}$ |
| Si—CH$_3$ | 1255 cm$^{-1}$ |
| vinyl | 890 cm$^{-1}$ |

Iodine number: 11

EXAMPLE 6

The polybutadiene of Example 2 (54 g) is reacted with 22 mg of platinum ethylene pyridine dichloride and 57.4 g of triethoxysilane in toluene at 100° C. The product has an ethoxy value of 41.4%. This corresponds to a conversion of 0.33 butadiene units.

This compound (103 g) is mixed with 350 g of $C_4H_9$—(O—$R^7$)$_{13.8}$OH and 250 g of $C_4H_9$—(O—$R^6$)$_{7.7}$OH (C:O ratio of $R^6O=2.8:1$; of $R^7O=2.1:1$) as a 50% solution in toluene as well as with 0.7 g of butyl titanate, heated for 1 hour under reflux and then freed from volatile components, initially at atmospheric pressure and later under vacuum. A yellowish liquid (514 g) with the following analytical data is obtained:

Elementary analysis: Found: Si 1.2%; C 60.9%; Calculated: Si 1.4%; C 60.3%.

IR bands as in Example 2, without Si—CH$_3$

Iodine number: 25

EXAMPLE 7

$C_4H_9$—(O—$R^7$)$_{36.9}$OH (36 g) and 36 g of $C_4H_9$—(O—$R^6$)$_{33.8}$OH (C:O ratio of $R^6O=2.5:1$, of $R^7O=2.2:1$) are distilled azeotropically in 110 g of toluene. The solution is allowed to cool and 17.4 g of trimethylchlorosilane are added. After refluxing for 1 hour, the volatiles are removed at 100° C. in the vacuum produced by a water-jet pump.

The remaining liquid is mixed with a solution of 5.8 g of the polybutadiene/methyldichlorosilane adduct of Example 2 in 50 ml of toluene, as well as with 0.6 g of dodecylbenzenesulfonic acid. The solution is subsequently heated to 100° C. under vacuum until there is no further distillate, diluted with 100 ml of toluene, and, after addition of 1.7 g of triethylamine, filtered. The solvent-free, highly viscous product (57 g) is slightly yellowish and has a PMW of 65,000 with a somewhat wider molecular weight distribution than the compounds synthesized by the method of Examples 1 to 6.

Elementary analysis: Found: Si 0.9%; C 58.7%; Calculated: Si 0.7%; C 59.1%.

IR bands as in Example 2.

COMPARISON EXAMPLES 8 TO 10

For comparison, the polyesters $C_4H_9$—(O—$R^7$)$_{36.9}$OH, $C_4H_9$—(O—$R^6$)$_{33.8}$OH and $C_4H_9$—(O—$R^8$)$_{31}$OH (C:O ratio of $R^6O=2.5:1$; of $R^7O=2.2:1$; of $R^8O=3:1$) are each reacted separately in a similar manner with the polybutadiene/methyldichlorosilane adduct of Example 2 according to the teachings of German Pat. No. 23 21 557.

EMULSION BREAKING EXPERIMENTS

The compounds from Examples 1 to 10 were tested for their activity with a German crude oil containing 48% water. For this purpose, 20 ppm of the different substances were added to a calibrated sight glass containing in each case, 50 ml of the crude oil and the amount of water in ml which had settled out after certain times, was noted. During the whole of the experiment, the temperature was kept constant at 50° C.

In the following table, Examples 8 to 10 are not of the invention. Even in mixtures, the polyethers themselves, which were used for the synthesis of the products, are at best, only slightly active and are therefore not shown.

| WATER (ml) WHICH HAS SETTLED OUT AFTER THE TIME INDICATED | | | | |
|---|---|---|---|---|
| | 0.5 hour | 1 hour | 2 hours | 3 hours |
| In accordance with the invention. | | | | |
| Example 1 | 20 | 22 | 22 | 23 |
| Example 2 | 18 | 21 | 22 | 22 |
| Example 3 | 18 | 20 | 20 | 21 |
| Example 4 | 18 | 19 | 21 | 21 |
| Example 5 | 20 | 20 | 20 | 22 |
| Example 6 | 19 | 20 | 21 | 21 |
| Example 7 | 18 | 21 | 21 | 22 |
| Not in accordance with the invention. | | | | |
| Example 8 | 2 | 3 | 7 | 9 |
| Example 9 | 3 | 4 | 9 | 13 |
| Example 10 | 0 | 0 | 0 | 0 |

A comparison of the emulsion breakers of Example 1 to 7 with those of Examples 8 to 10 which are not in accordance with the invention, shows that the presence in the organosilicon-modified polydienes of two polyethers, which differ clearly in their hydrophilic or hydrophobic character, leads to a significant improvement in breaking the emulsion of crude oil.

We claim:

1. Organosilicon-modified polydienes having the formula:

(I)

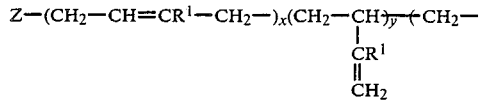

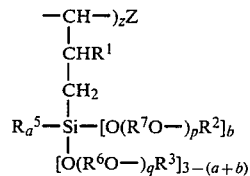

$R_a^5$—Si—[O(R$^7$O—)$_p$R$^2$]$_b$
       [O(R$^6$O—)$_q$R$^3$]$_{3-(a+b)}$ in which
  Z represents a chain terminating group,
  R$^1$ is a hydrogen or methyl radical,
  R$^2$, R$^3$, and R$^4$ are lower alkyl radicals with 1 to 4 carbon atoms, which can be the same or different within the polymeric molecule,
  R$^5$ is a methyl radical or the O—(R$^8$O—)$_s$—R$^4$ group;
  R$^6$, R$^7$, R$^8$ are alkylene radicals with 2 to 4 carbon atoms,
  a is 0 to 2,
  2 < b < 3, whereby 0 < a+b < 3,
  p, q, s ≧ 2,
  x, y ≧ 0, and
  z ≧ 3 and wherein the C:O ratio of R$^6$O is 2.25 to 3:1, the C:O ratio of R$^7$O is 2 to 2.75:1, the C:O ratio of R$^8$O is 2 to 3:1, the difference in the C:O ratio of R$^6$O and R$^7$O is not less than 0.25 and the C:O ratio of R$^8$O is less than that of R$^7$O or greater than that of R$^6$O.

2. The polydienes of claim 1 wherein the sum of x and y is 25 to 80 mole percent of the sum of x, y and z.

3. The polydienes of claim 1 having the formula:

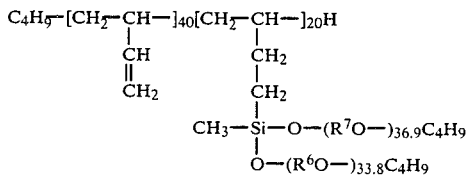

wherein
  C:O ratio of R$^6$O = 2.5:1,
  C:O ratio of R$^7$O = 2.2:1;

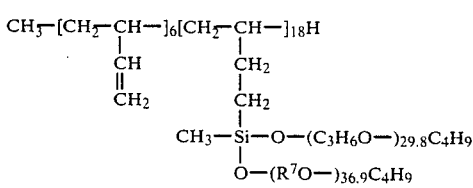

wherein
  C:O ratio of R$^6$O = 3:1,
  C:O ratio of R$^7$O = 2.2:1;

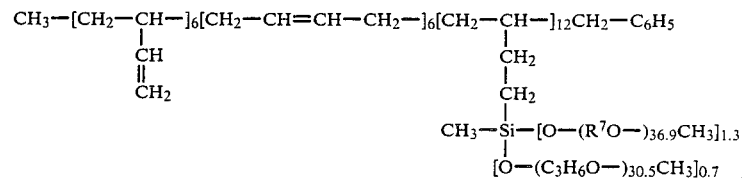

wherein
  C:O ratio of R$^5$O = 3:1,
  C:O ratio of R$^7$O = 2.2:1, or

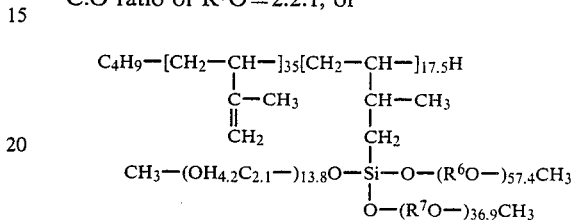

wherein
  C:O ratio of R$^6$O = 2.5:1,
  C:O ratio of R$^7$O = 2.2:1.

4. The polydienes of claim 1 wherein Z is selected from the group consisting of —H, CH$_2$=CH—CH$_2$—CH$_2$—, —CH$_2$—CH$_2$—OH, —COOH, —CH$_3$, —C$_4$H$_9$, —C$_6$H$_5$, —CH$_2$—CH$_6$H$_5$, and —Si(CH$_3$)$_3$.

5. A process for the synthesis of compounds of claim 1 wherein at least z moles of silanes having the formula (CH$_3$)$_a$SiHX$_{3-a}$ in which X is a halogen, alkoxy or acyloxy radical, are added to polydienes having the formula

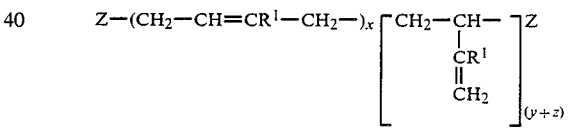

which have a molecular weight of 300 to 200,000 in the presence of noble metal catalysts and reacting the addition products obtained with a reactant selected from the group consisting of
  (a) a mixture consisting of at least two polyoxyalkylene monools and which contains b.z moles of an optionally trimethylsilylated polyoxyalkylene monool having the formula HO(R$^7$O—)$_p$R$^2$ and (3—a—b)z moles of a polyoxyalkylene monool having the formula HO(R$^6$O—)$_q$R$^3$ or
  (b) consecutively with these monools, and polyoxyalkylene trimethylsilyl esters.

6. A process for the synthesis of compounds of claim 2 wherein at least z moles of silanes having the formula (CH$_3$)$_a$SiHX$_{3-a}$ in which X is a halogen, alkoxy or acyloxy radical, are added to polydienes having the formula

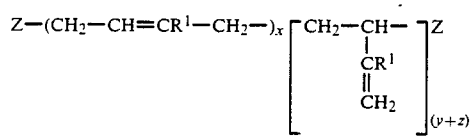

which have a molecular weight of 300 to 200,000 in the presence of noble metal catalysts and reacting the addition products obtained with a reactant selected from the group consisting of (a) a mixture consisting of at least two polyoxyalkylene monools and which contains b.z moles of an optionally trimethylsilylated polyoxyalkylene monool having the formula

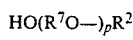

and (3—a—b)z moles of a polyoxyalkylene monool having the formula $$HO(R^6O-)_qR^3$$

or (b) consecutively with these monools, and polyoxyalkylene trimethylsilyl esters.

7. The process of claim 5 wherein polyoxyalkylene trimethylsilyl esters are reacted instead of the polyoxyalkylene monools.

8. The process of claim 6 wherein polyoxyalkylene trimethylsilyl esters are reacted instead of the polyoxyalkylene monools.

9. Use of compounds of claim 1 as emulsion breakers for crude oil/water emulsions.

10. Use of compounds of claim 2 as emulsion breakers for crude oil/water emulsions.

* * * * *